(12) United States Patent
Barbieri et al.

(10) Patent No.: US 6,794,659 B2
(45) Date of Patent: Sep. 21, 2004

(54) RAPID HIGH THROUGHPUT SPECTROMETER AND METHOD

(75) Inventors: Beniamino Barbieri, Champaign, IL (US); Enrico Gratton, Urbana, IL (US)

(73) Assignee: I.S.S. (USA) Inc., Champaign, IL (US)

(*) Notice: Subject to any disclaimer, the term of this patent is extended or adjusted under 35 U.S.C. 154(b) by 0 days.

(21) Appl. No.: 10/454,875

(22) Filed: Jun. 4, 2003

(65) Prior Publication Data

US 2003/0206297 A1 Nov. 6, 2003

Related U.S. Application Data

(62) Division of application No. 09/621,248, filed on Jul. 21, 2000, now Pat. No. 6,603,546.

(51) Int. Cl.[7] .............................................. G01N 21/64

(52) U.S. Cl. .................................................... 250/459.1

(58) Field of Search ................................ 356/317, 318, 356/419; 250/458.1, 459.1, 461.1, 461.2

(56) References Cited

U.S. PATENT DOCUMENTS 6,455,861 B1    9/2002   Hoyt ........................... 356/318
6,498,017 B2 * 12/2002   Riesner et al. ................. 435/23

OTHER PUBLICATIONS

S.R. Aragon, et al: "Fluorescence Correlation Spectroscopy and Brownian Rotational Diffusion": Biopolymers, vol. 14, pp. 119–138 (1975).

K M Berland, et al . "Scanning Two–Photon Fluctuation Correlation Spectroscopy: particle Counting Measurements of Detection for Molecular Aggregation"; Biophysical Journal. vol. 71, Jul. 1996, pp. 410–420.

Keith M. Berland, et al.: "Two–Photon Fluorescence Correlation Spectroscopy: Method and Application to the Intracellular Environment"; Biophysical Journal, Vol 68, Feb. 1995, pp. 694–701.

Julian Borejdo: Motion for MyosinFragments During Actin–Activated ATPase: Fluroescence Correlation Spectroscopy Study. Biopolymers. vol. 18, pp. 2807–2820 (1979).

Yan Chen, et al "The Photon Counting Histogram in Fluorescence Fluctuation Spectroscopy"; Laboratory for Fluorescence Dynamics, University of Illinois at Urbana–Champaign, Urbana, Illinois USA. Updated Version: May 15, 1998.

(List continued on next page.)

Primary Examiner—F. L. Evans
(74) Attorney, Agent, or Firm—Garrettson Ellis; Seyfarth Shaw LLP

(57) ABSTRACT

A fluorescence spectrometer comprises a laser and at least one beam splitter positioned to receive a light beam from the laser and to divide it into several first light beam portions. Dichroic mirrors are positioned to separately receive the first light beam portions and to reflect the beam portions at an angle to the first light beam portions. Transparent chambers are provided for holding the samples. Objective lens systems are respectively positioned in the path of the reflected beam portions to respectively focus each reflected beam portion to a point within one of the separate transparent chambers. Lenses are positioned to receive fluorescence from a sample for testing within the transparent chambers and to respectively focus the fluorescence at pin holes in opaque partitions. The lenses are positioned to receive the fluorescence, which passes back through the objective lens system and the dichroic mirror. Light detectors are each respectively positioned adjacent to one of the partitions, with one of the partitions respectively positioned between each of the lens and the light detectors to permit each light detector to sense fluorescence through the pin hole. Electronics are provided to receive and process signals from each light detector. Structure is provided to permit high speed data collection from a large number of samples in separate, transparent chambers.

4 Claims, 4 Drawing Sheets

OTHER PUBLICATIONS

C. Egeling, et al.; "Monitoring Conformational Dynamics of a Single Molecule by Selective Fluorescence Spectroscopy"; PubMed Central,m Proc. Natl. Acad. Sci. USA, vol. 95, Issue 4, pp. 1556–1561, Feb. 17, 1998: Biophysics.

M. Ehrenberg, et al,. "Rotational Brownian Motion and Fluorescence Intesity Fluctuations". Chemical Physics 4, (1974). pp. 390–401.

Manfred Eigen, et al. "Sorting Single Molecules: Application to Diagnostics and Evolutionary Biotechnology", Proc. Natl. Acad. Sci. USA, vol. 91, pp. 5740–5747, Jun. 1994.

Elliot L Elson "Fluorescence Correlation Spectroscopy. I. Conceptual Basis and Theory"; Biopolymers, vol. 13, pp. 1–27 (1974).

E. Jakeman, et al "The Twinkling of Stars"; Contemp. Phys., 1978, vol. 19, No. 2, pp. 127–145.

J.B. Johnson: "Thermal Agitation of Electricity in Conductors"; Physical Review, Jul. 1928, vol. 32.

P. Kask, et al. "Separation of the Rotational Contribution in Fluorescence Correlation Experiments"; Biophys. J., Biophysical Society, vol. 55, Feb. 1989; pp. 213–220.

Dennis E Koppel, "Statistical Accuracy in Fluorescence Correlation Spectroscopy", Physical Review A, vol. 10, No. 6.

D. E. Koppel et al. "Dynamics of Fluorescence Marker Concentration as a Probe of Mobility"; Biophysical Journal, vol. 16, 1976.

Dennis E. Koppel. et al.: "Scanning Concentration Correlation Spectroscopy Using the Confocal Laser Microscope"; Biophysical Journal, vol. 66, Feb. 1994, pp. 502–507.

Douglas Magde et al. "Thermodynamic Fluctuations in a Reacting System—Measurement by Fluorescence Correlation Spectroscopy", Physical Review Letters, vol. 29, No. 11. Sep. 11, 1972.

Douglas Magde: "Fluorescence Correlation Spectroscopy. II. An Experimental Realization"; Biopolymers, vol. 13, pp. 29–61 (1974).

L. Mandel "Sub–Poissonian Photon Statistics in Resonance Fluorescence"; Optics Letters, Jul. 1979; vol. 4, No. 7.

Ulrich Meseth, et al.: "Resolution of Fluorescence Correlation Measurements"; Biophysical Journal, vol. 76, Mar. 1999; pags. 1619–1631.

Arthur G. Palmer III et al. "Molecular Aggregation Characterized High Order Autocorrelation in Fluorescence CorrelationSpectroscopy"; Biophysical Journal, vol. 52. Aug. 1987; pp. 257–270.

Arthur G. Palmer III, et al. "High–order Fluorescence Fluctuations Analysis of Model Protein Clusters"; Proc. Natl. Acad. Sci USA. vol. 86, pp. 6148–6452, Aug. 1989 Biophysics.

Hong Qian "On the Statistics of Fluorescence Correlation Spectroscopy"; Physical Chemistry, 38 (1990), pp. 49–57.

Hong Qian, et al. "Distribution of Molecular Aggregation by Analysis of Fluctuation Moments"; Proc. Natl. Acad. Sci. USA, vol. 87, pp. 5479–5483, Jul. 1990; Biophysics.

Hong Qian et al. "On the Analysis of High Order Moments of Fluorescence Fluctuations"; Biophysical Journal, Vol 57, Feb. 1990; pp. 375–380.

Hong Qian et al. "Analysis of Confocal Laser–Microscope Optics for 3–D Fluorescence Correlation Spectroscopy": Applied Optics. Apr. 1, 1991; vol. 30, No. 10.

Barbara Rauer et al. Fluorescence Correlation Spectrometry of the Interaction Kinetics of Tetramethylrhodamin a–bungarotoxin with Torpedo California Acetylcholine Receptor, Biophysical Chemistry, 58, (1996), pp. 3–12.

Rudolf Rigler, et al. "2. Interactions and Kinetics of Single Molecules as Observed by FluorescenceCorrelation Spectroscopy"; Department of Medical Biophysics. Box, 60400, S. 10401 Stockholm, Sweden.

Petra Schwille et al. "Dual–Color Fluorescence Cross–Correlation Spectroscopy for Multicomponent Diffusional Analysis in Solution"; Biophysical Journal, vol. 72, Apr. 1997, pp. 1878–1886.

Nancy L Thompson, "Fluorescence Correlation Spectroscopy"; Topics in Fluorescence Spectroscopy, vol. 1, Techniques, edited by Joseph R. Lakowicz. Plenum Press, New York, 1991.

Nancy L Thompson et al. "Immunoglobulin Surface–Binding Kinetics Studied by Total Internal Reflection with Fluorescence Correlation Spectroscopy"; Biophysical Journal, vol. 43, Jul. 1983; pp. 103–114.

M. Weissman et al. Determination of Molecular Weights by Fluctuation Spectroscopy: Application to DNA:; Proc Natl Acad Sci USA, vol. 76, No. 8, pp. 2776–2780; Aug. 1976; Biophysics.

Jerker Widengren et al. "Fluorescence Correlation Spectroscopy of Triplet States in Solution A Theoretical and Experimental Study"; J. Phys. Chem. 1995, 99, pp. 13368–13379.

* cited by examiner

RAPID HIGH THROUGHPUT SPECTROMETER AND METHOD

This is a division of U.S. patent application Ser. No. 09/621,248, filed Jul. 21, 2000 now U.S. Pat. No. 6,603,546.

BACKGROUND OF THE INVENTION

The invention relates to improvements in a multiple channel spectrometer capable of quickly analyzing large volumes of samples by the fluorescence emitted by the samples. While many different systems for causing fluorescence emission and processing of the fluorescence may be used, one currently preferred method is known as fluorescence correlation spectroscopy (also known as fluorescence fluctuation spectroscopy). Examples of this technique are as described in Schrof et al. U.S. Pat. No. 5,815,262. Other examples of fluorescence cross-correlation spectroscopy are shown in the articles by Andre Koltermann et al. from the *Proceedings of the National Academy of Science*, Volume 95, pages 1421–1426, February 1998 entitled "Rapid Assay Processing by Integration of Dual Color Fluorescence Cross-Correlation Spectroscopy: High Throughput Screening for Enzyme Activity"; and the article by Petra Schwille et al. from the *Biophysical Journal*, Volume 72, pages 1878–1886, April 1997, entitled "Dual Color Fluorescence Cross-Correlation spectroscopy for Multi Component Diffusional Analysis Solution".

In the Schrof et al. U.S. Pat. No. 5,815,262, fluorescence correlation spectroscopy (FCS) is described in which an excitation laser beam passes through a series of wells (sample chambers) arranged in linear array. The beam is refocused prior to entering each sample chamber, so that fluorescence takes place in a very small area, which area is monitored and sensed to obtain fluorescence data simultaneously from a plurality of samples.

With such a technique, difficulties have been found in the refocusing of light after the laser beam has passed through the first well or sample chamber. Also, possible change of the laser light beam may take place as it passes through the various, separate samples, which may effect the data obtained from particularly the "downstream" samples in the linear array. Also, two photon excitation, as is used in the above cited patent, generally requires a very expensive laser, while one photon excitation permits the use of cheaper lasers.

Additionally most of the prior art systems utilize a conventional hardware correlator to receive the raw data from multiwell plates in fluorescence correlation spectroscopy. Data from the hardware correlator is passed to the computer processing unit for determination of the parameters of interest, which may include diffusion coefficients and the concentrations of the components. However, several limitations hinder the use of a hardware correlator in this manner. Specifically, when a particulate or an aggregate is present in the solution being analyzed, and it passes through the tiny region illuminated by the focused laser beam, the entire calculated autocorrelation function resulting from the data has to be rejected, as it is altered by the temporary presence of the particulate or aggregate. As the result, the measurement on that specific well from where the data comes has to be rejected, and, more likely, measurement of the entire multiwell plate has to be acquired again.

Also, the raw data may contain useful information and features that are completely and definitively lost once the data has been processed through the hardware correlator. By system of this invention, the user can examine the raw data after they have been acquired. Specifically, it may turn out that higher order correlation functions may be of more interest in describing the molecular interactions occurring in the sample solutions being analyzed through the spectrometer. Thus, if one can keep the raw data, this permits the user to further analyze it with more complicated analysis models when that is desired.

The analysis can be easily implemented in an automated fashion by properly designed software for a spectrometer, particularly for high throughput screening instruments.

Also, the first order autocorrelation function of fluorescence correlation spectroscopy is typically determined by using the time-mode, which is the traditional way of calculating the function. See particularly Thompson, Fluorescence Correlation Spectroscopy, in "*Topics in Fluorescence Spectroscopy*", Volume 1 (J. R. Lakowicz, Editor), Plenum Press, New York 1991, pages 337–410. Time mode operations tend to limit the precision in determining concentrations, and increase the data acquisition time.

It is desired to perform drug and other screening at very large rates of analysis. For example, current techniques can allow screening up to 50,000 to 100,000 compounds a day. However, it should be desirable in the field of high throughput screening to significantly increase the capacity of spectrometers to process large numbers of compounds. Many of the current high throughput screening apparatus are manufactured by L. J. L. Biosystems of Sunnyvale, Calif.; Aurora Biosciences of San Diego, Calif.; Molecular Devices of Sunnyvale, Calif.; and Packard Instruments of Meriden, Conn.

Fluorescence emission is usually preferred for such high throughput uses due to the overall sensitivity when compared to other techniques such as absorption measurements. Another advantage of using fluorescence is the detection method of availability of a range of fluorophores that can be used as extrinsic probes. Typically, five parameters can be measured when using a fluorescence technique, namely the intensity of the excitation spectra, the intensity of the emission spectra (each at selected wavelengths), the polarization of the excitation spectrum, the quantum yield of fluorescence, and the decay time of the excited level.

Fluorescence correlation spectroscopy was originally proposed by Magde et al., Thermodynamic Fluctuations in a Reacting System: Measurements by Fluorescence Correlation Spectroscopy, *Physical Review Letters*, Volume 29 (1972), pages 705–708. In this technique, the temporal fluctuations of the detected fluorescence signal (that is time-dependent, spontaneous intensity fluctuations of the fluorescence signal in the typically tiny observation volume) are detected and analyzed to obtain information about the processes occurring on a molecular scale. These intensity fluctuations and the volume under observation may arise from Brownian motion, flow, and chemical reactions. During the past years, fluorescence correlation spectroscopy has been utilized to measure transitional diffusion coefficients, rotational diffusion coefficients, kinetic rate constants, molecular aggregation, and molecular weights. An article by Thompson et al., presents a review of the technique (N. L. Thompson et al., Fluorescence Correlation Spectroscopy, in "*Topics in Fluorescence Spectroscopy*", Volume 1 (J. R. Lakowicz, Editor Pleanum Press, New York 1991, pages 337–410).

DESCRIPTION OF THE INVENTION

By this invention, an apparatus and method are provided for carrying out high throughput screening of active compounds, typically using fluorescence correlation spectroscopy, although other techniques may be utilized making use of this invention. A fluorescence probe is excited through a one photon or multi photon excitation process. The light source may be lamp such as an xenon arc or deuterium lamp, or a laser such as continuous wave lasers: i.e., argon-ion, krypton-ion, helium-neon, helium-cadmium, or other lasers. Pulsed lasers may also be used such as nitrogen lasers or mode-locked lasers, diode lasers, or lasers placed in an array. In each of the possible radiation sources, the light source should be capable of delivering radiation at a particular wavelength or wavelengths that excite the fluorescence probe through one photon or multi photon excitation processes. Typically, such excitation wavelengths may range from 200 nm. to 5,000 nm.

By this invention, a fluorescence spectrometer is provided which comprises a laser; and at least one beam splitter (which may be a prism-type beam splitter, a fiber optic system, or similar device for accomplishing the beam splitting function) positioned to receive a light beam from the laser and to divide the beam into a plurality of separate, first light portions. Thus, multiple first light beam portions are provided, typically spaced from and extending parallel to each other.

Dichroic mirrors are positioned to separately receive the first light beam portions and to reflect the beam portions at an angle to the first light beam portions, typically perpendicular. A plurality of transparent wall chambers (such as wells) are provided for holding samples to be analyzed. Typically, a conventional multiple well sample plate may be used. Objective lens systems are provided (typically for confocal use), for example microscopes, which systems are respectively positioned in the path of each of the reflected first beam portions, to respectively focus each reflected beam portion to a point within one of the separate, transparent chambers, to elicit a fluorescent response from the sample for testing in the chamber.

Lenses are respectively positioned to receive the fluorescence from the sample for testing (which samples are within the transparent chambers), and to respectively focus the fluorescence at pinholes in respective, opaque partitions. The lenses are positioned to receive the fluorescence which passes back through the objective lens system and the dichroic mirror, and then to focus the fluorescence at a respective pinhole. The dichroic mirror is selected so that it is transparent to at least one wavelength of the fluorescence.

Light detectors are each respectively positioned adjacent to one of the pinholes, with that pinhole being respectively positioned between the lens and the light detector of the particular system, to permit each light detector to sense fluorescence through the pinhole. Electronics are then provided to receive and process signals from each light detector.

The spectrometer of this invention will comprise a plurality of such individual systems, typically four or eight, for simultaneous processing of sample in separate chambers or wells, to contribute to a high throughput system.

Typically, a plate comprises the transparent chambers described above, plus a plurality of other transparent chambers for holding samples, typically carried by the same plate. An x-y movement device carries the plate and permits a first group of the chambers to be respectively and simultaneously exposed to the first light beam portions for analysis of the resulting fluorescence. Then, the x-y device may be moved in a two dimensional, planar manner for exposure of another group of chambers of the plate to the first light beam portions, for their analysis.

Preferably, the system is set up so that fluorescence from each transparent chamber which passes through the objective lens system and the dichroic mirror extends in a straight line, passing further through the objective lens system and the pinhole to the light detector in the same straight line.

Accordingly, all array of such detector systems, comprising the above items to control and process multiple first beam portions, can be used to systematically and simultaneously analyze the contents of multiple chambers of a plate, followed by translation of an x-y table which carries the plate, for analysis of another set of the chambers, until the multiple chamber plate (up to 384 or more such chambers) has been completely and rapidly analyzed. By way of advantage, each of the first beam portions produced by this invention pass through only one chamber and sample per individual analysis, so there is no possibility of chamber data cross contamination resulting from a light beam that passes through multiple chambers to elicit a fluorescent response, as in the patent cited above.

Preferably, the light excitation and detection scheme used in this invention follows the confocal design of microscopy. Data acquisition can be achieved by measuring the time intervals between the photons reaching the detector and building a histogram of the detected counts. The volume in the sample from which photons are detected can be of extremely small volume, for example, about 0.1 to 10 femtoliters, which is on the order of the volume of a bacterium. The photon counting histogram provides the concentrations of the molecular species present in the solution and the number of photons emitted by each species. The invention can also derive simultaneously the autocorrelation function or higher-order correlation functions of the parameters of interest for rapid high throughput. Screening can be acquired on such small observation volumes over a time of about one to five seconds. Direct measurement of single molecules and the kinetics involved over any desired time scale can be achieved by this technique. The lower limit of detection is due to impurities and buffer contamination, plus the effect of the particulate resulting from insoluble compounds.

Thus one can perform fluorescence correlation spectroscopy by acquiring a fluorescence measurement from a sample over time to obtain a histogram of photon counts; deriving the molecular brightness of at lest one molecular species in the sample; and determining he concentration of the species from the data obtained.

Data acquisition and analysis of the data may comprise the steps of: acquiring a fluorescence measurement over time from a sample in the form of electronic raw data. This electronic raw data may be picked up by a light detector, sent to a preamplifier discriminator, and then sent to a computer, where the raw data may be stored, in accordance with this invention, and contrary to the procedure used with the conventional hardware correlator.

The electronically stored raw data is then processed using a first algorithm, without erasing the electronically stored, original raw data. Then, as an advantage of and by means of this invention, the stored raw data may be reprocessed using one or more additional algorithms, or the data may be reprocessed with the first algorithm, without the need of acquiring a complete set of new data as may be required in the prior art.

In fluorescence correlation spectroscopy (FCS), the fluorescence signal F(t) as a function of time is measured as the raw data. The temporal autocorrelation of the fluorescence fluctuations, which is a measurement of the average temporal duration of the fluorescence fluctuations, is determined. Typically, the normalized autocorrelation function is defined as:

$$G(\tau) = \frac{\langle \delta F(t+\tau) \delta F(t) \rangle}{\langle F(t) \rangle^2} \quad (1)$$

G(τ) decays in time. The rate of the decay and the shape of the Curve contain information about the mechanisms and the rates of the processes that generate the fluorescence fluctuations. The observed fluctuations of the fluorescence signal obey Poisson statistics with the amplitude of the average fluctuation proportional to $N^{1/2}$, where N represents the number of molecules in the observation volume. Nanomolar concentrations can be detected. Using FCS with two-photon excitation, the observation volume ranges typically from 0.1 to $1.0 \times 10^{-15}$ liters (or femtoliter, abbreviated as "fl"). This small observation volume allows the direct measurement of single molecules and the kinetics involved over a time scale extending from hundreds of nanoseconds to seconds or hours. The lower limit of detection is due to impurities and buffer contamination and the effect of the particulate generated from insoluble compounds.

It is generally preferred to acquire the data using a photon-mode technique rather than a time mode technique, although either method may be used in accordance with this invention.

In the photon mode technique, as is known per se, the detector records the time delay between one photon and the next photon from the fluorescence arriving to the detector. In this implementation of the data acquisition, the "clocks" are the events to be recorded, and the photons are the starts-stops which define each interval.

On the other hand, in time mode techniques, the detector counts the number of photons collected from the sample in a specific time interval. Typically, the instrument uses about 256 different time intervals. The length of a time interval is specified by the user through the software which controls the operation. Thus, the photons are the "events" to be recorded at each time interval. The "clocks" are the arbitrary starting and ending stops defined by the electronics to create each desired time interval.

By way of advantage, the method of this invention may be used in conjunction with a one photon excitation technique, in which the excited level of the molecule is created by one photon contrary to the situation where two or more photons are needed to create the necessary excitation to achieve fluorescence in the sample. One photon excitation techniques can use significantly less expensive lasers.

In this invention, a data acquisition card may be provided in the computer used for processing the data, in which the data acquisition card acquires the raw data from the light detector and arranges for its storage in the computer memory. Then, the computer may calculate the desired autocorrelation function or higher-order correlation functions. This provides the advantage that bad data may be eliminated without losing the entire data set pertinent to the sample well under examination, contrary to the situation of a hardware correlator. The bad data may result from the presence of a solid particle in the tiny volume being examined for fluorescence. Additionally, the raw data may be rerun after acquisition for recalculation based on higher order correlation functions, if that is needed. Such a data acquisition card can also have the capability of acquiring the data in either the time mode or in the photon mode, as may be desired.

Also, as previously discussed, rapid, multiple, simultaneous analysis of sample chambers may take place in accordance with this invention for high volume screening operations.

DESCRIPTION OF SPECIFIC EMBODIMENTS

Figure 1:
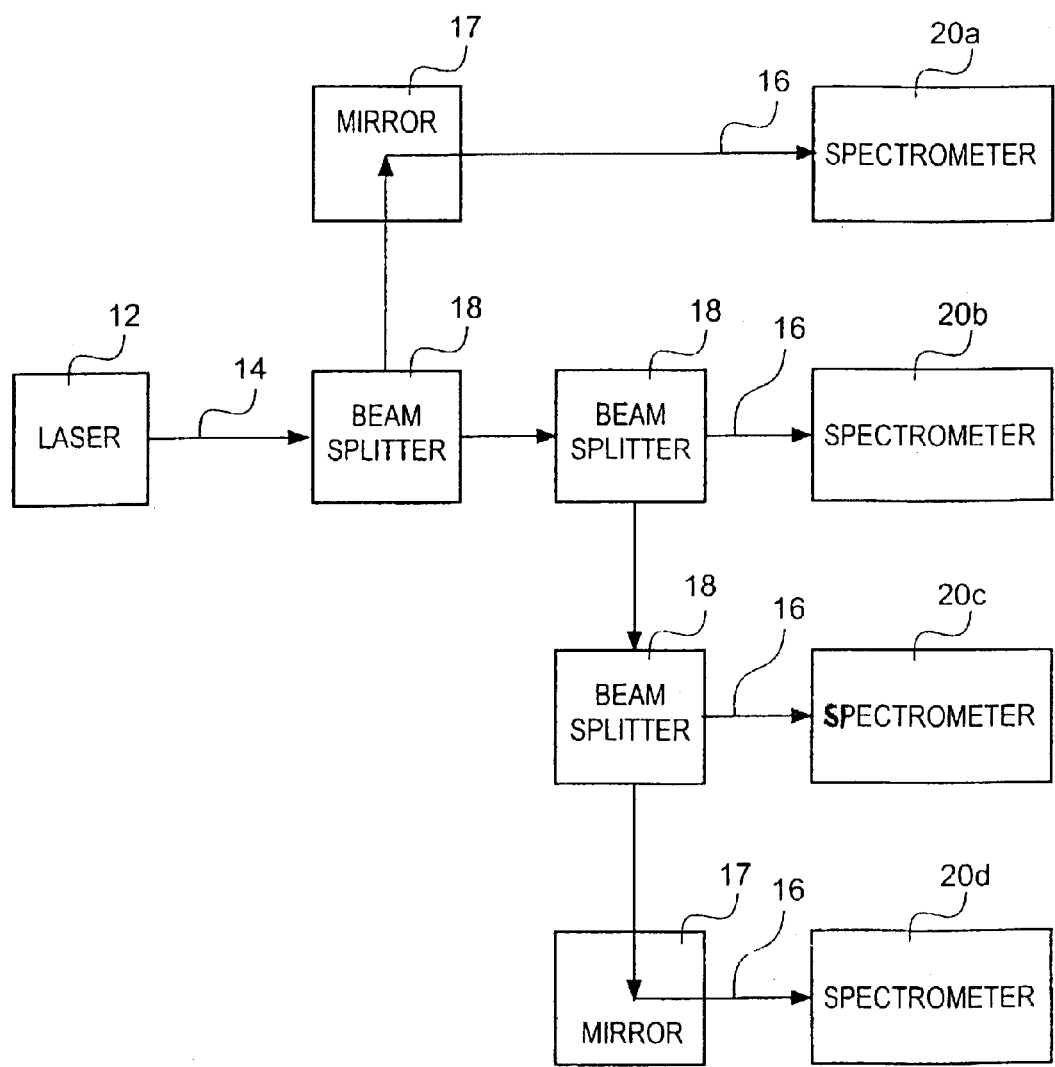
FIG. 1 is a schematic view of a fluorescent spectrometer for FCS, shown in a plan view.

Referring to FIG. 1, a multi-channel high throughput screening (HTS) spectrometer 10 is shown in schematic form, used for FCS.

A laser 12 serves as a source of excitement radiation for fluorescent samples. Light beam 14 from laser 12 is split into four separate first light beam portions 16 by a group of beam splitters 18 of conventional design and mirrors 17. The first light beam portions 16 respectively enter different spectrometer units 20a, 20b, 20c, 20d for the irradiation of separate samples and the sensing of fluorescence emitted from the samples. The detailed structure of the spectrometer units 20a–20d may be identical, one being specifically shown in FIG. 3.

Alternatively, the system of beam splitters 18 and angle mirrors 17 may be replaced by a multiple light cable system, in which light is transmitted from the laser by the cable system to provide individual first light beam portions directed to the respective spectrometer units 20a–20d.

There is no intrinsic limit on the number of individual spectrometer units 20 which may be irradiated by a single laser 12. For example, at least eight separate spectrometer units may be serviced by laser 12 and a light distribution system 17, 18 (or light cables), up to about 150 spectrometer units and more if desired, depending upon the power of the laser.

Figure 2:
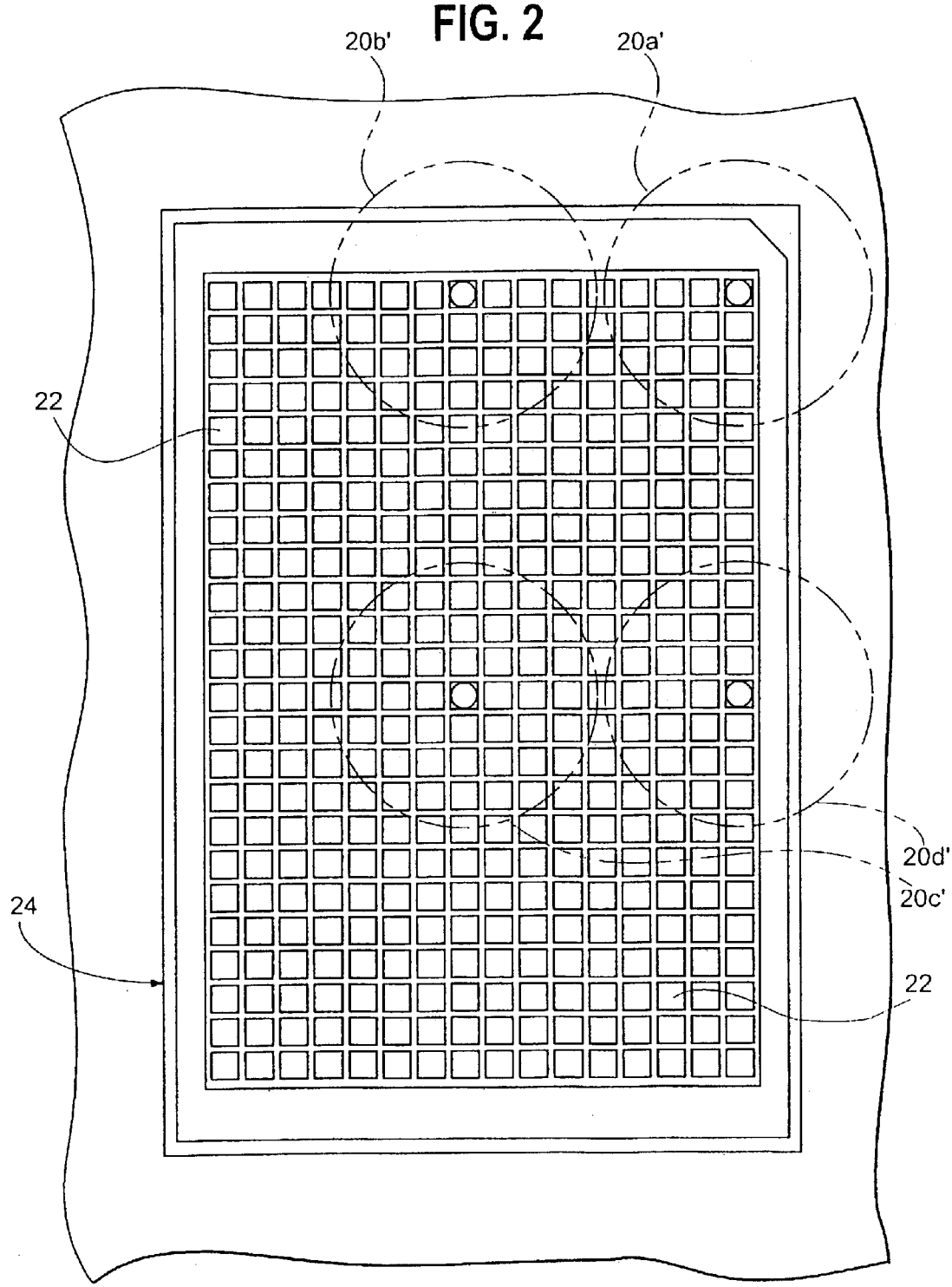
FIG. 2 is a partially schematic bottom plan view showing the four spectrometer units similar to the units of FIG. 1 but in a rectangular, not a linear arrangement, and their relationship with a microwell plate for holding the samples.

FIG. 2 shows a plan view of a system which is basically identical with FIG. 1 except that the respective, corresponding spectrometer units 20a', 20b', 20c', 20d' are arranged in a square rather then a straight line pattern by appropriate modification of the light distribution system 17, 18 (or light cables). The spectrometer units point at the transparent bottoms of chambers 22, which are present in a checkerboard array as part of a commercially available 384 well plate 24, so that 384 separate samples may be analyzed by the fluorescence spectrometer of this invention. Plate 24 is carried in an open bottom X-Y table 26, which is capable of precise movement in both horizontal directions, so that after a typical 1–5 second irradiation of the four wells 22 that are being analyzed by the respective spectrometer units 20a'–20d', X-Y table 26 can be horizontally shifted so that four new wells 22 may then be tested by the four spectrometer units. Accordingly, the system of this invention is capable of high volume production of spectrographic analysis of a large number of samples. X-Y tables are well-known, commercially available devices.

Figure 3:
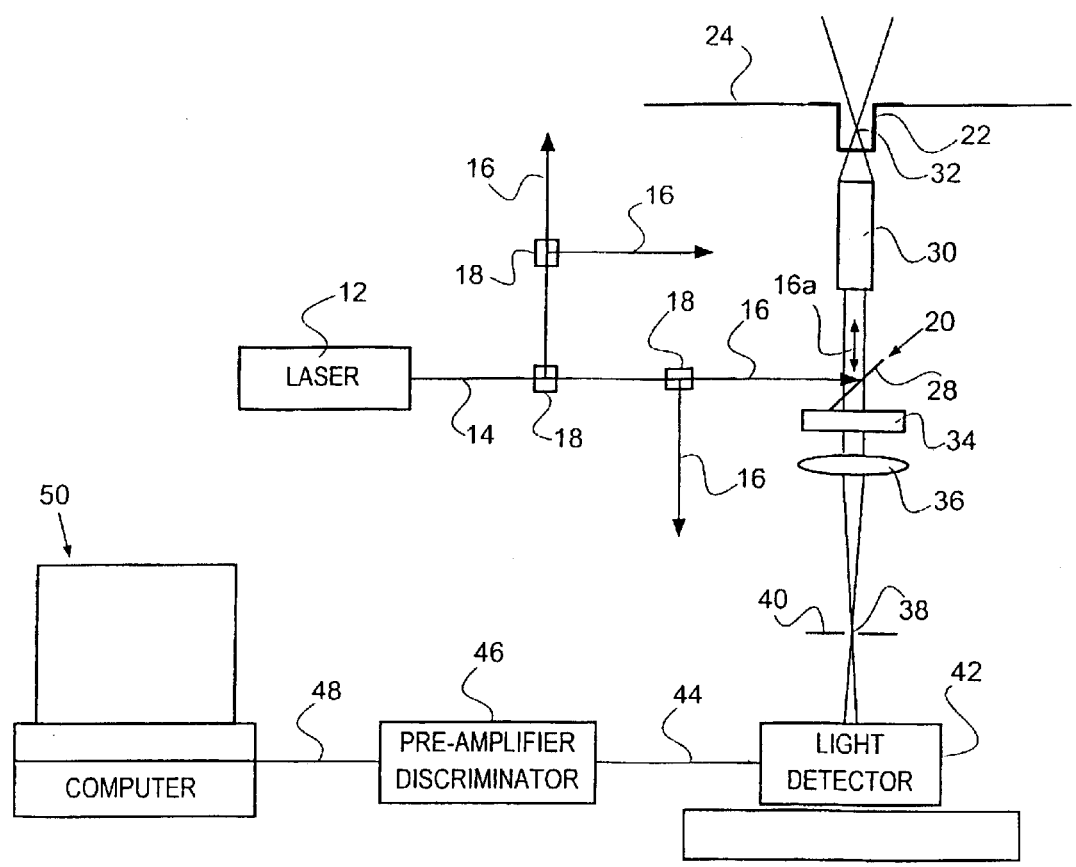
FIG. 3 is an elevational schematic view of a single spectrometer unit, for simultaneous use along with other similar spectrometer units in the device of FIG. 1 or 2.

Referring to FIG. 3, an elevational view of the various spectrometer units 20, and their design, may be seen. Laser 12 emits light beam 14, which light beam is repeatedly split by a light distribution system comprising a series of beam splitters 18, to form the respective separate, first light beam portions 16, as in FIG. 1. By the appropriate arrangement of beam splitters 18 [and diagonal mirrors 17, as desired], first light beam portions 16 may be directed in any pattern desired, linear, rectangular, or otherwise for transfer into spectrometer units 20.

As shown, one of the beam portions 16 enters unit 20 and strikes dichroic mirror 28, being reflected upwardly as a beam portion 16a. Dichroic mirror 28 is a commercially available mirror having the characteristic of being reflective to light at some wavelengths and transmissive to light at other wavelengths. Of course, first light beam portion 16 is selected to be of a wavelength that is reflected by dichroic mirror 28.

Light beam 16a passes through objective 30, which generally functions as a microscope, focusing the light beam to a focal point 32 residing within microwell 22 and within the sample contained therein. As previously stated, the volume at focal point 32 can cover a very small volume of material, on the order of a one femtoliter volume approximating the volume of a bacterium. The laser intensity is adjusted so that photo bleaching of the sample is avoided, resulting from excessive beam intensity. The optimum beam intensity depends upon the sample concentration plus the sample quantum yield, which is the number of photons emitted by the sample divided by the number of photons passed into the sample. Some fluorophores may have a very low quantum yield, which naturally will then require a larger laser beam intensity.

The fluorescent response may take place from one or more of the molecules within the tiny, focused volume 32, the fluorescence being at a characteristic wavelength that is typically different from the wavelength of the laser beam 16, 16a. Some of this fluorescence passes back through objective lens 30 and through dichroic mirror 28 without much reflection, since it is of a different wavelength. The dichroic mirror is of a type selected to be transparent to the particular fluorescent wavelength. It is desirable for the fluorescence to pass back through the same objective lens 30 that the irradiating radiation passes through in the other direction, since when a second objective lens is used, it would be difficult for the second objective lens to align and focus upon the same volume 32 that the first objective lens 30 is focusing on.

After passing through the dichroic mirror 28, filter 34 blocks light of wavelengths other than the desired wavelengths. The fluorescent light is focused by lens 36, so that it passes through a pinhole 38 in an opaque partition 40 at or very near the focal point of lens 36 under the particular conditions.

The amount of the volume of sample probed by the instrument (typically at the femtoliter range) is determined by the optics of the system, plus the diameter of pin hole 38. If desired, an instrument incorporating this invention may carry a series of different pinholes which may be alternatively placed into the position shown in FIG. 3, to provide a variation of the volume of sample 22 thus probed by spectrometer unit 20.

A light detector 42 of conventional design is monitoring pinhole 38 from the other side of partition 40. When light is detected, it will be typically only fluorescence from the sample, since other wavelengths of light are removed by filter 34. Signals from the light detector 42 pass through cable or wire 44 to preamplifier discriminator 46, and the signals from discriminator 46 pass through cable or wire 48 to computer 50. In the computer, the fluorescent signal, measured as a function of time, is processed to obtain a temporal autocorrelation of the fluorescence fluctuations, which is a measurement of the average temporal duration of the fluorescence fluctuations. Using the well-known normalized autocorrelation function, it becomes possible to directly measure fluorescence characteristics of single molecules, and the kinetics involved over a time scale extending from hundreds of nanoseconds to seconds or hours.

Figure 4:
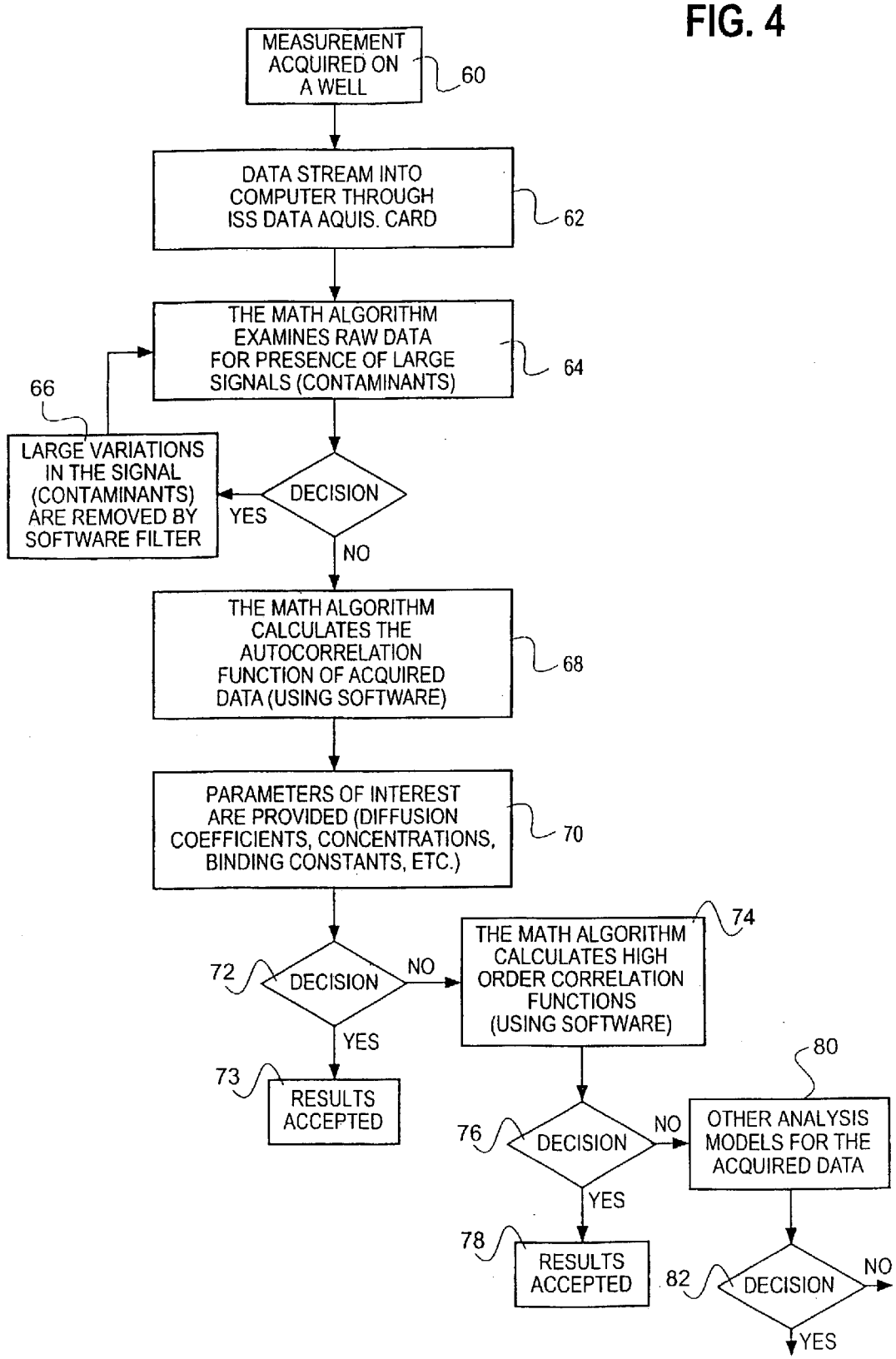
FIG. 4 is a flow chart for software processing of data obtained with the devices of FIGS. 1–3.

Referring to FIG. 4, the data is processed by means of the above technique as follows: the measurement 60 is acquired on a well 22 in the manner previously described. The data passes as a data stream into computer 50 as at 62. A math algorithm 64 examines the raw data for the presence of large signal variations indicating contaminants. If present, large variations in the signal are removed by a software filter 66, and the data passes through math algorithm 64 again. If no large signal variations are found, a math algorithm 68 calculates the autocorrelation function of the acquired data. Parameters of interest are determined, such as diffusion coefficients, concentrations, binding constants, etc. through software 70.

At decision point 72 of the flowchart, results are either accepted in accordance with predetermined criteria of algorithm 73. If the criteria are not achieved, the math algorithm 74 calculates higher order correlation functions through the computer software. Again a decision point 76 is reached. If the results are now in compliance with the criteria of the algorithm 78, the results are accepted and provided to the user. Otherwise, the algorithm may be predetermined to provide another analysis model 80 for the acquired data. This recursive loop of decisions including decision point 72, 76, 82 may continue for as long as may be desired, until the results fit the desired criteria or there are no other algorithms or analysis techniques available in the program to process the data.

By such techniques, a wide variety of studies of the behavior of matter, living and otherwise, can be performed. The translational mobility of cytoplasm in living cells on latex beads can be determined. Additionally, the presence of chemical complexes and their proportional concentration, compared with the separate reactants can be measured. Drugs and other chemicals can be screened for their presence or absence. Also, a wide variety of theoretical studies for physical chemistry and the like can be performed.

Specifically, the use of the above apparatus and method may be optimized by the algorithms discussed below:

In high throughput screening (HTS) applications important parameters are the sensitivity and the capability to separate productive species from background signal and unproductive species fast and efficiently. Until recently, most of the methods employed either were slow or have very low efficiency. The analysis of fluorescence from single molecules could open a new avenue for sensitivity and selectively. The major concept in this field is how to analyze signals from different molecular entities. If the molecules of interest are fluorescent, the methods of single molecule detection and analysis can provide a powerful new way to perform an analysis of the sample on a molecule-per-molecule basis. To achieve this goal, 1) we must restrict the analysis volume to the conditions that one or at most few molecules be present in that volume, 2) we must collect very efficiently the fluorescence emitted from that small volume, 3) we must devise fast on-line algorithms to analyze the fluorescence signals and sort the results according to the different molecular populations present in the sample. Since the fluorescence properties are analyzed on the flight, there is in principle no limit on the number of different fluorescence population that we can separate: the actual limit is given by the signal-to-noise ratio. For example, using this principle of molecular sorting, we can separate one bright molecule from a large number of dim fluorescent molecules even if the concentration of the bright molecule is very low compared to the dim molecules. It is precisely this principle that we are applying to the HTS apparatus to increase the sensitivity and the speed of data analysis. In reality, it is not always possible to reduce the concentration of the fluorescent molecules to the limit in which only one molecule is present in the analysis volume and the analysis of the statistics of the observed fluorescence signal requires complex mathematical methods. However, we were able to reduce the mathematical complexity to simple formulas that can be handled by modern computers to allow on-line analysis. In the following we describe how we achieve the 3 conditions outlined above for this new method to work Small Volume.

We have exploited the confocal principle and/or multiphoton excitation to achieve fluorescence excitation volume which are diffraction limited. The volumes that can be obtained using current state-of-the-art microscopy objectives and common lasers are on the order of 0.1 fL. A volume of that size contains on the average 0.06 molecules for a sample at a concentration of 1 nM. These concentrations are typical in HTS applications.

Efficient Light Collection.

We are using relatively high numerical aperture objectives and a particular cell for HTS that allow us to use short working distance objective. Also the light detector we use (avalanche photo diode) has very high quantum efficiency in the spectral region of most dyes used in HTS. We also use relatively high excitation power to saturate the absorption of the dye. Absorption saturation is easily obtained using conventional lasers both in one or multi-photon excitation. As a consequence we can routinely obtain counting rates exceeding 100000 counts/sec/molecule. During the fluorescent burst when a dye molecule is under the laser beam which last on the order of 1 ms or longer, assuming that the dye is attached to a macromolecule, we collect on the average about 50–100 photons. This number of photons collected is sufficient to provide statistics for the separation of dye molecule which differ in brightness by about a factor of 2.

One can analyze the distributions of photon count histograms (PCH), to analyze on line complex situations in which more than one molecule is present in the excitation volume.

Additional Considerations.

The apparatus we assembled allows the simultaneous measurement of the fluorescence signals using two light detectors. Therefore, it is possible in principle to measure two separate spectroscopic properties such as differential wavelength emission and polarization of a molecule. The principles described below can very well adapt to a multiple detector system Description of the Theory Fluctuation experiments observe a physical process that is stochastic in nature. The time series of such a random signal can be rather complex. Consequently, an analysis based on statistical methods is required to examine stochastic processes (Gardiner, 1985). Traditionally, FCS experiments determine the autocorrelation function $g(\tau)$ from the sequence of photon counts in order to examine the statistics of the time-dependent decay of the fluorescence intensity fluctuations to their equilibrium value. The determination of the autocorrelation function from the raw data is a data reduction technique. Hence, some information encoded in the time series of the photon counts is lost. While the autocorrelation approach is the method of choice for characterizing kinetic processes embedded in the stochastic signal, it lacks information regarding the amplitude distribution of the intensities (Bendat and Piersol, 1971). Here we consider a different data analysis approach based on the amplitude distribution of the fluorescent intensities. Experimentally photon counts rather than intensities are measured and the statistics of the photon count amplitudes must be considered. We are specifically interested in the probability to observe k photon counts per sampling time. This probability distribution of photon counts is experimentally determined by the photon counting histogram (PCH). The analysis of fluorescence fluctuation experiments by PCH had been recently introduced by our group (Chen et al., 1999). In this contribution, we focus on the theoretical foundation of the photon counting histogram and its experimental realization. We develop the theory for a single fluorescent species and confirm it experimentally. In addition we apply the PCH method to separate heterogeneous sample compositions. Therefore, the theory is generalized to include multiple species. The autocorrelation function $g(\tau)$ describes the fluctuations in the tine domain, but with the exception of $g(0)$ lacks amplitude information. The photon counting histogram, on the other hand, characterizes the amplitude distribution of the fluctuations, but lacks kinetic information. Thus, autocorrelation and PCH analysis are complementary techniques and PCH should be able to separate a mixture of species based on a brightness difference between the components regardless of their diffusion coefficients. We discuss the use of PCH to separate a mixture of components and consider sample conditions, such as the molecular brightness and the particle concentration. We demonstrate the technique by resolving a binary dye mixture from the photon count distribution. Furthermore, we apply PCH analysis to a mixture of biomolecules with either one or two fluorescent labels attached and resolve them experimentally.

Theory

To describe the PCH of a freely diffusing species we first consider a single, diffusing particle enclosed in a small box of volume $V_0$. The PCH of a single particle depends explicitly on the beam profile of the excitation light. In the next step, several particles are added to the box and the corresponding PCH function determined. To describe an open system with Poissonian number fluctuations, the boundary condition of the volume is removed and particles are allowed to enter and leave the box. We expanded the model to cover multiple species and calculate the PCH for a number of beam profiles. However, first we consider the statistics of the photon detection process.

PCH and the Theory of Photon Detection

Fluorescence fluctuation experiments are typically performed using single photon counting techniques. Each detected photon gives rise to an electric pulse, which is sent to the data acquisition system. Thus, the fluorescence intensity reaching the photodetector is converted into photon counts. The photon detection process changes the statistics of the measured intensities by adding shot noise to the photon counts (Saleh, 1978). For example, a constant light intensity at the detector $I_D$ gives rise to a Poissonian distribution of photon counts k, $$Poi(k, \langle k \rangle) = \frac{(\eta_I I_D)^k e^{-\eta_I I_D}}{k!}. \tag{1}$$

Shot noise is a random Poisson point process, and reflects the discreteness and statistical independence of the photoelectric detection process (Snyder, 1975). The factor $\eta_1$ is the proportionality factor between the average photon counts $\langle k \rangle$ and the constant intensity $I_D$ at the detector, $\langle k \rangle = \eta_1 I_D$. It incorporates the detection efficiency and the sampling time interval. The variance $\langle \Delta k^2 \rangle$ of a distribution serves as an indicator of its width. For the Poisson distribution, the mean and the variance are equal, $\langle \Delta k^2 \rangle = \langle k \rangle$.

A Poisson distribution describes the photon count statistics for light of constant intensity. Fluctuations in the light intensity change the photon counting statistics and the corresponding distribution of photon counts was first described by Mandel (Mandel, 1958), $$p(k) = \int_0^\infty Poi(k, \eta_I I_D) p(I_D) dI_D. \tag{2}$$

The probability of observing k photoelectron events is given by the Poisson transformation of the intensity probability distribution $p(I_D)$. However, to be more precise, photon detection involves a short, but finite sampling time $\Delta t_s$, which along with the detector area A needs to be integrated over to yield the energy W, $$W(t) = \int_t^{t+\Delta t_s} \int_A I(r, t) dA dt. \tag{3}$$

Thus, technically we observe energy fluctuations of the collected light, rather than intensity fluctuations. However, if the time scale of the intensity fluctuations is longer than the sampling time $\Delta t_s$, then the energy fluctuations track the intensity variations. We will assume for the rest of the paper that the sampling time $\Delta t_s$ is chosen fast enough, so that the energy fluctuations track the intensity fluctuations of interest. We also assume a stationary process, so that there is no explicit time dependence to the statistical properties of the photon counts, and a detector area A small enough, so that the intensity field is essentially constant across the detector surface.

Mandel's formula (eq. 2) essentially describes a superposition of Poissonian distributions scaled by the respective probability of the intensity distribution function $p(I_D)$. The photon count distribution $p^{(k)}$ is now characterized by a variance $\langle \Delta k^2 \rangle$ greater than its mean value, $\langle \Delta k^2 \rangle > \langle k \rangle$, which is classified as super-Poissonian (Teich and Saleh, 1988). Thus, intensity fluctuations lead to a broadening of the photon count distribution with respect to a pure Poisson distribution (FIG. 1). The variance $\langle \Delta I_D^2 \rangle$ of the intensity distribution $p(I_D)$ determines the variance of the photon counts $\langle \Delta k^2 \rangle = \langle k \rangle + \langle \Delta I_D^2 \rangle$ (Mehta, 1970). Thus, as the strength of the intensity fluctuations increases, so does the broadening of the photon counting histogram. The changes in the shape of the histogram from a Poisson distribution are characteristic for the intensity distribution $p(I_D)$ and it is possible to infer some characteristic properties of the light source from the photon counting histogram. This approach has been used in the past to investigate the scattering of light (Bertolotti, 1973), the twinkling of stars (Jakeman et al., 1978) and the fluctuations of laser light (Risken, 1970). Here we follow the same approach and directly model the photon counting histogram to describe fluorescence fluctuation experiments of freely diffusing particles.

The experimental setup typically involves a microscope and an objective, that is used to focus the excitation light in order to achieve a small spatial volume. A detector collects the fluorescent light emerging from the excitation volume. The effect of the microscope optics and the detector on the shape of the observation volume is characterized by the point-spread function (PSF) of the instrument. The shape of the PSF influences the photon count distribution and will be considered for a few PSF conventionally used in confocal and two-photon detection (Qian and Elson, 1991; Berland et al., 1995). In our context, it is more convenient to define a scaled PSF, $\overline{PSF}$, such that the volume of the scaled PSF, $V_{PSF} = \int \overline{PSF}(\vec{r}) d\vec{r}$, is equal to the volume defined for FCS experiments (Thompson, 1991).

PCH of a Single Particle

We consider a single particle diffusing in an enclosed box with a volume $V_0$ large enough, so that it essentially contains the PSF (FIG. 2a). Based on Mandel's formula we derived an equation which expresses the photon count distribution as a function of the PSF (Chen et al., 1999), $$p^{(1)}(k; V_0, \varepsilon) = \int Poi(k, \varepsilon \overline{PSF}(\vec{r})) p(\vec{r}) d\vec{r} = \frac{1}{V_o} \int_{V_o} Poi(k, \varepsilon \overline{PSF}(\vec{r})) d\vec{r}, \tag{4}$$

where $p(\vec{r})$ describes the probability to find the particle at position $\vec{r}$. For a freely diffusing particle, the probability equals $1/V_0$ inside the box and zero outside of the box. The photon counting probability $p^{(1)}(k; V_0, \varepsilon)$ for a single particle enclosed in a volume $V_0$ depends on the shape of the PSF and the parameter $\varepsilon$. The meaning of this parameter is best illustrated by considering the average photon counts $\langle k \rangle$ of the PCH $p^{(1)}(k; V_0, \varepsilon)$, $$\langle k \rangle = \frac{\varepsilon}{V_o} \int_{V_o} \overline{PSF}(\vec{r}) d\vec{r} = \varepsilon \frac{V_{PSF}}{V_o}. \tag{5}$$

The average photon counts are thus determined by the product of $\varepsilon$ and the probability to find the molecule within the volume of the point spread function $V_{PSF}$. Therefore $\varepsilon$ describes the molecular brightness, which determines the average number of photon counts received during the sampling time $\Delta t_s$ for a particle within the observation Volume $V_{PSF}$. The average photon counts received $\langle k \rangle$ scale linearly with the sampling time. Therefore, the ratio $\varepsilon_{sec} = \varepsilon / \Delta t_s$ is independent from the somewhat arbitrary sampling time $\Delta t_s$. The parameter $\varepsilon_{sec}$ expresses the molecular brightness in photon counts per second per molecule (cpsm) and allows a more convenient comparison between different experiments.

PCH of Multiple Particles

Now let us consider N independent and identical particles diffusing inside a box of volume $V_0$ (FIG. 2b). If one could follow a particular particle individually, the PCH of this particle would be given by $p^{(1)}(k; V_0, \varepsilon)$ according to eq. 5. For N independent particles the corresponding PCH, $p^{(N)}(k; V_0, \varepsilon)$, is given by consecutive convolutions of the single particle PCH functions $p^{(1)}(k; V_0, \varepsilon)$ (Feller, 1957), $$p^{(N)}(k; V_0, \varepsilon) = \underbrace{(p^{(1)} \otimes \ldots \otimes p^{(1)})}_{\text{N-times}}(k; V_0, \varepsilon). \tag{6}$$

PCH of Particles with Number Fluctuations

The assumption of a closed system, in which particles diffuse inside a box, does not describe the experimental situation, unless the reference volume includes the whole sample. But a macroscopic reference volume would require the evaluation of an astronomical number of convolutions according to eq. 6. Instead, we choose to consider an open system in which particles are allowed to enter and leave a small sub-volume (FIG. 2c). The sub-volume is in contact with a much larger reservoir volume and the distribution of the number of particles N inside the sub-volume is given by a Poisson distribution (Chandrasekhar, 1943), $$p_N(N)=Poi(N,\bar{N}), \quad (7)$$

where $\bar{N}$ describes the average number of molecules within the reference volume $V_0$. Of course if there are no particles in the reference volume, no photon counts are generated and we define the corresponding PCH as, $$p^{(0)}(k; V_0, \varepsilon) = \delta(k), \quad \text{with } \delta(k) = \begin{cases} 1, k = 0 \\ 0, k > 0 \end{cases}. \quad (8)$$

Now we can express the PCH for an open system $\hat{p}(k;V_0, \bar{N},\epsilon)$ as the expectation value of the N-particle PCH $p^{(N)}(k;V_0;\epsilon)$ considering Poissonian number statistics, $$\Pi(k;\bar{N}_{PSF},\epsilon)\equiv\hat{p}(k;V_0,\bar{N},\epsilon)=\langle p^{(N)}(k;V_0,\epsilon)\rangle_N. \quad (9)$$

The PCH function $\hat{p}(k;V_0,\bar{N},\epsilon)$ describes the probability to observe k photon counts per sampling time for an open system with an average of $\bar{N}$ particles inside the reference volume $V_0$. The particular choice of the reference volume for an open system is irrelevant. It is intuitively clear, that the properties of an open system have to be independent of the arbitrary reference volume $V_0$ (Chen et al., 1999). Thus, the photon count distribution should be either referenced to an intensive quantity, like the particle concentration, or to some standard volume. We choose the convention used in FCS, where the volume of the PSF, $V_{PSF}$, connects the g(0) value of the autocorrelation function to the average number of molecules $\bar{N}_{PSF}$ (Thompson, 1991). Consequently we drop the $V_0$ parameter dependence for the PCH of an open system and declare a new function $\Pi(k;\bar{N}_{PSF}, \epsilon)$, which characterizes the PCH of an open system referenced to the volume of the PSF. The average number of photon counts $\langle k \rangle$ can be calculated from eq. 9 and is given by the product of the molecular brightness $\epsilon$ and the average number of particles $\bar{N}_{PSF}$ inside the PSF volume, $$\langle k \rangle = \epsilon \bar{N}_{PSF}. \quad (10)$$

PCH of Multiple Species

So far, only identical particles have been treated. Often more than one type of particle is present in the sample. It is straightforward to expand the theory under the assumption that the particles are non-interacting. Let us consider the case of two different species for simplicity. If we could distinguish the photon counts emerging from each species, we could directly determine the PCH of each species, $\Pi(k;\bar{N}_1,\epsilon_1)$ and $\Pi(k;\bar{N}_2,\epsilon_2)$. However, we cannot distinguish the origin of the photon counts. But as long as the photon emission of both species is statistically independent, the PCH of the mixture is given by the convolution of the photon count distributions of species 1 with the one of species 2, $$\Pi(k;\bar{N}_1,\bar{N}_2,\epsilon_1,\epsilon_2)=\Pi(k;\bar{N}_1,\epsilon_1)\otimes\Pi(k;\bar{N}_2,\epsilon_2). \quad (11)$$

For more than two species all single species photon counting distributions are convoluted successively to yield the photon count distribution of the mixture.

PCH for Different PSFs

The photon count distribution depends on the PSF. Here we report the PCH of a single particle $p^{(1)}(k;V_0,\epsilon)$ for a few PSF of interest. The Gaussian-Lorentzian squared PSF has been used to describe the two-photon excitation beam profile for our experimental conditions (Berland et al., 1995), $$\overline{PSF}_{2GL}(\rho, z) = \frac{4\omega_o^4}{\pi^2 \omega^4(z)} \exp\left[-\frac{4\rho^2}{\omega^2(z)}\right]. \quad (12)$$

The PSF is expressed in cylindrical coordinates and the excitation profile has a beam waist $\omega_0$. The inverse of the Lorentzian along the optical axis for an excitation wavelength of $\lambda$ is given by, $$\omega^2(z) = \omega_o^2\left(1 + \left(\frac{z}{z_R}\right)^2\right), \quad \text{with } z_R = \frac{\pi\omega_o^2}{\lambda}. \quad (13)$$

To calculate the PCH of a single particle for a reference volume $V_0$, eq. 12 is inserted into eq. 4, but integrated over all space. Integrating over all space is mathematically convenient and ensures the correct PCH for the open volume case, since from a mathematical point of view the PSF extends to infinity. However, the PCH of a closed volume is only approximately determined. The quality of the approximation depends on the size of the reference volume $V_0$. If the volume is chosen so, that the contribution of the PSF to the photon counts is negligible outside of the reference volume, then the deviation between both functions is small. However, the PCH of a closed volume so is from a practical point of view only of minor interest, since the PCH of an open volume describes the experimental situation. We refer the interested reader to a more detailed discussion of this point by Chen et al. (Chen et al., 1999). The PCH of a single particle is then determined for k>0 by a one-dimensional integral $$p^{(1)}_{2GL}(k; V_0, \varepsilon) = \frac{1}{V_0} \frac{\pi^2 \omega_o^4}{2\lambda k!} \int_0^\infty (1 + x^2) \gamma\left(k, \frac{4\varepsilon}{\pi^2(1+x^2)^2}\right) dx, \text{ for } k > 0. \quad (14)$$

The integral, which contains the incomplete gamma function $\gamma$ (Abramowitz and Stegun, 1965), can be evaluated numerically.

A second important PSF is the three dimensional Gaussian PSF, which is used extensively to describe confocal detection (Qian and Elson, 1991; Rigler et al., 1993a), $$\overline{PSF}_{3DG}(x, y, z) = \frac{I(x, y, z)}{I_0} = \exp\left[-\frac{2(x^2 + y^2)}{\omega_0^2} - \frac{2z^2}{z_0^2}\right], \quad (15)$$

with an effective beam waist $z_0$ in the axial direction. The PCH of a single particle is determined in the same way as for the other PSF and we derive for k>0 an expression in the form of a one-dimensional integral, $$p^{(1)}_{3DG}(k; V_0, \varepsilon) = \frac{1}{V_0} \frac{\pi \omega_o^2 z_0}{k!} \int_0^\infty \gamma\left(k, \varepsilon e^{-2x^2}\right) dx, \text{ for } k > 0. \quad (16)$$

For the measurement of surface processes the PSF is typically approximated by a two-dimensional Gaussian, $$\overline{PSF}_{2DG}(x, y) = \frac{I(x, y)}{I_0} = \exp\left[-\frac{2(x^2 + y^2)}{\omega_0^2}\right], \quad (17)$$

and the corresponding PCH is given by, $$p_{2DG}^{(1)}(k; A_0, \varepsilon) = \frac{1}{A_0} \frac{\pi \omega_0^2}{2k!} \gamma(k, \varepsilon), \quad \text{for } k > 0. \quad (18)$$

Here we reference of course to an area $A_0$ instead of to a volume. Finally, if the PSF is uniform, then the PCH is simply a Poisson distribution, $p_U^{(1)}(k; V_{PSF}, \varepsilon) = \text{Poi}(k, \varepsilon)$.

Describing PCH with the Moment Generating Function

The PCH of a single particle has just been described for photon counts k>0. To evaluate the PCH for k=0 one must determine the sum over all photon counts k>0 and subtract it from the area of the probability distribution, which is normalized to one, $$p^{(1)}(0) = 1 - \sum_{k=1}^{\infty} p^{(1)}(k).$$

Furthermore, the computation of the PCH for each photon count requires a numerical integration.

We now introduce an alternative formalism to determine the probability distribution of photon counts using a moment generating function. This approach not only determines the photon count probability for zero photon counts directly, but also expresses the single particle PCH in form of an analytical expression. The description is based on a formal relationship between the Laplace and Poisson transform. The Laplace transform L and the Poisson transform P are formally defined as, $$P(n) = P[f(x)] = \int dx \, f(x) \frac{x^n e^{-x}}{n!}, \quad (19)$$

$$F(s) = L[f(x)] = \int dx \, f(x) e^{-sx}.$$

The Laplace transform F(s) of the probability function f(x) is also its moment generating function (Saleh, 1978), $$\langle f^n \rangle = (-1)^n \frac{\partial^n F(s)}{\partial s^n}\bigg|_{s=0}. \quad (20)$$

The Poisson transform can be expressed in terms of the Laplace transform F(s) through the following relationship (Saleh, 1978), $$P(n) = \frac{(-1)^n}{n!} \frac{\partial^n F(s)}{\partial s^n}\bigg|_{s=1} \quad (21)$$

Often the Poisson transform can be calculated for n=0 or 1 in closed form. For example, for the squared Gaussian-Lorentzian PSF, we get the following result for n=1, $$p_{2GL}^{(1)}(1) = \varepsilon r_2 F_2\left[\begin{array}{cc} 1/4, & 3/4 \\ 1/2, & 2 \end{array} \bigg| -\frac{4}{\pi^2} s\varepsilon\right]\bigg|_{s=1} = (-1)\frac{\partial F(s)}{\partial s}\bigg|_{s=1}, \quad (22)$$

with $r = \frac{V_{PSF}}{V_0}$.

The properties of the generalized hypergeometric function $_pF_q$ are described in the literature (Slater, 1966; Luke, 1969). The zeroth moment of a probability distribution is equal to one, therefore the moment generating function satisfies the condition, F(0)=1, according to eq. 20. We can determine the moment generating function F(s) from eq. 22, $$F(s) = 1 + r\frac{8}{3}\left(1 - {}_2F_2\left[\begin{array}{cc} -3/4, & -1/4 \\ -1/2, & 1 \end{array} \bigg| -\frac{4}{\pi^2} s\varepsilon\right]\right). \quad (23)$$

The photon counting histogram can now be determined from the moment generating function according to eq. 21, using the analytical form of the derivatives of the generalized hypergeometric function and the notation $(\alpha)_k$ for the Pochhammer function, $$p_{2GL}^{(1)}(k) = \left(1 + r\frac{8}{3}\left(1 - {}_2F_2\left[\begin{array}{cc} -3/4, & -1/4 \\ -1/2, & 1 \end{array} \bigg| -\frac{4}{\pi^2}\varepsilon\right]\right)\right), \text{ for } k = 0 \quad (24)$$

$$p_{2GL}^{(1)}(k) = \left(\frac{2}{\pi}\right)^{2k} \frac{\varepsilon^k}{k!} r\frac{8}{3} \frac{(-3/4)_k(-1/4)_k}{(-1/2)_k(1)_k} {}_2F_2\left[\begin{array}{cc} -3/4+k, & -1/4+k \\ -1/2+k, & 1+k \end{array} \bigg| -\frac{4}{\pi^2}\varepsilon\right], \text{ for } k < 0.$$

By using the moment generating function to describe the PCH of a single particle we arrive at an analytical solution for $p_{2GL}^{(1)}$ including k=0.

A second example for the use of the moment generating function is illustrated for the homogeneous PSF. In this case, a Poisson distribution determines the PCH of a single particle. The PCH for an open system is described by a compound Poisson distribution, $$\Pi(k; \bar{N}, \varepsilon) = \sum_{N=0}^{\infty} \text{Poi}(k, \varepsilon N) \text{Poi}(N, \bar{N}). \quad (25)$$

Instead of evaluating the sum in eq. 25 one can use a moment generating function to determine the PCH. Here we use the factorial moment generating function Q(s) of the compound Poisson distribution, $$Q(s) = e^{(e^{-s\varepsilon} - 1)\bar{N}}. \quad (26)$$

The moment generating function Q(s) allows us to calculate the PCH of the open system analytically by using the following relationship, $$\Pi(k; \overline{N}, \varepsilon) = \frac{(-1)^k}{k!} \frac{d^k}{ds^k} Q(s)|_{s=1}. \qquad (27)$$

Twofold PCH Statistics

The photon count distribution characterizes the amplitude fluctuations of the detected photons, but lacks kinetic information. We want to demonstrate how to expand the theory of PCH to include time dependence and show how PCH is related to the autocorrelation function of FCS experiments. The photon count distribution considered so far describes the number of detected photons in a single time interval. However, by studying the joint statistics of photon counts from two short time intervals separated by a time delay $\tau$, we incorporate time-dependence to the photon count statistics (Saleh, 1978). Here we specifically consider the two-fold distribution of photon counts for a diffusing particle. The conditional probability that a particle at position $\overline{r}_0$ at time $t_0$ will be found at a later time $t_1$ at position $\overline{r}_1$ is given by the solution of the diffusion equation (see for example (Chandrasekhar, 1943)), $$p_d(\overline{r}_0(t_0)|\overline{r}_1(t_1)) = (4\pi D\tau)^{\frac{-3}{2}} e^{\frac{(\overline{r}_1 - \overline{r}_0)^2}{4D\tau}}, \qquad (28)$$

where D is the diffusion coefficient of the particle and $\tau$ the time difference $t_1 - t_0$. In the following we only consider time lags $\tau > 0$ to avoid the complication of shot noise correlations at $\tau = 0$. The photon Count probability $p(k, \overline{r}_0)$ for a particle with molecular brightness $\epsilon$ at position $\overline{r}_0$ is given by a Poisson distribution, $p(k, \overline{r}_0) = \text{Poi}(k, \epsilon \text{PSF}(\overline{r}_0))$. The average photon counts $\langle k(\overline{r}_0) \rangle$ at position $\overline{r}_0$, is proportional to the fluorescence intensity $I(\overline{r}_0)$, $\langle k(\overline{r}_0) \rangle = \eta I(\overline{r}_0)$. The proportionality constant $\eta$ describes the detection efficiency and is set to 1 for simplicity. The probability $p^{(1)}(k_0, k_1; \epsilon, \tau)$ to observe $k_0$ photon counts at time $t_0$ and $k_1$ photon counts at a later time $t_1$ for a diffusing particle with brightness $\epsilon$ is then determined by (Qian, 1990), $$p^{(1)}(k_0, k_1; \epsilon, \tau) = \int \int d\overline{r}_0 d\overline{r}_1 p(\overline{r}_0) p(k_0, \overline{r}_0) p_d(\overline{r}_0(t_0)|\overline{r}_1(t_0 + \tau)) p(k_1, \overline{r}_1). \qquad (29)$$

where $p(\overline{r}_0)$ describes the probability to find the particle at position $\overline{r}_0$. The correlation function of the photon counts for a diffusing particle is equal to the correlation function of the fluorescence intensity, $$\langle k_0(t) k_1(t+\tau) \rangle = \sum_{k_o=0}^{\infty} \sum_{k_1=0}^{\infty} k_0 k_1 p^{(1)}(k_0, k_1; \varepsilon, \tau) = \qquad (30)$$

$$\int \int d\overline{r}_0 d\overline{r}_1 p(\overline{r}_0) I(\overline{r}_0) p_d(\overline{r}_0(t_0)|\overline{r}_1(t_1)) I(\overline{r}_1) = \langle I(t) I(t+\tau) \rangle$$

The above result was derived for a single particle, but it is straightforward to generalize the result to any number of particles or to an open volume with number fluctuations.

Data Analysis

We developed an algorithm to calculate the PCH $\Pi(k)$ based on the theory presented above and implemented it on a computer to fit experimental data. Photon counts are recorded with a home built data acquisition card, which is interfaced to a computer.

The computer calculates the histogram of the experimental data. The normalized histogram represents the experimental photon counting probability distribution $\tilde{p}(k)$. The statistical uncertainty associated with each element of $\tilde{p}(k)$ is determined by the standard deviation $\sigma_k = \sqrt{M\tilde{p}(k)(1-\tilde{p}(k))}$.

The number of data points M collected is typically of the order of $10^6$. The experimental data are fit by minimizing the reduced $\chi^2$-function, $$\chi^2 = \frac{\sum_{k=k_{min}}^{k_{max}} \left( M \frac{\tilde{p}(k) - \Pi(k)}{\sigma_k} \right)^2}{k_{max} - k_{min} - d} \qquad (31)$$

The experimental photon counts range from a minimum value $k_{min}$, which is typically 0 for most experiments, to a maximum number $k_{max}$, and the number of fitting parameters is given by d. The normalized residuals of the fit are determined by $$r(k) = M \frac{\tilde{p}(k) - \Pi(k)}{\sigma_k}.$$

Single Species PCH

We tested the theory of the photon counting statistics by comparing it to experiments. The numerical PCH algorithm was used to fit the experimental photon counting histograms to the theory as outlined in the data analysis section. The experiments were carried out using a two-photon setup and the details of the experiment are described in Chen (Chen, 1999). The measured photon counting distributions agree with the theoretical PCH functions calculated for the experimental setup within the statistical error. The molecular brightness $\epsilon$ and the average number of molecules shape the photon count distribution in characteristic ways. We first study the influence of the average number of molecules $\overline{N}$ upon the properties of the histogram.

Influence of the Particle Concentration

The photon count distribution of a fluorescein solution was measured at three different concentrations (FIG. 3). We performed a global fit of all three histograms with $\epsilon$ linked, while the average number of particles was allowed to vary. The data and the fitted histograms in FIG. 3 are in good agreement. The residuals between data and fit for each histogram are displayed in units of standard deviation $\sigma$. The residuals vary randomly and yield a reduced $\chi^2$ close to 1, indicating a good description of the data by the theoretical model. The recovered number of molecules $\overline{N}$ scales with the concentration of the sample. The dashed lines in FIG. 3 represent the corresponding Poisson distributions with a mean equal to the average photon counts $\langle k \rangle$ of the sample. The Poisson distribution approximates the PCH for the high fluorescein concentration case (FIG. 3a). However, lowering the dye concentration to 55 nM (FIG. 3b) already shows a broadening of the experimental PCH compared to the Poisson distribution, which is clearly visible in the tail of the distributions. The deviation of the PCH from a Poisson distribution becomes even more apparent by reducing the fluorescein concentration to 5.5 nM (FIG. 3c).

Thus, the photon counting histogram approaches a Poisson distribution with increasing fluorophore concentration. This behavior can be readily understood by considering the influence of the molecule concentration on the intensity fluctuations. The relative strength of the number fluctuations is given by the ratio between the standard deviation $\sigma$ and the mean $\mu$ of the particle number distribution, $$\frac{\sigma}{\mu} = \frac{\sqrt{\langle \Delta N^2 \rangle}}{\overline{N}} = \frac{1}{\sqrt{\overline{N}}}. \quad (32)$$

The number of molecules inside a small, open volume is Poisson distributed, and the relative strength of the particle fluctuations decreases with the inverse square root of the average number of particles $\overline{N}$. Thus with increasing particle concentration the number distribution approaches a delta function $\delta(N-\overline{N})$. Consequently, the fluctuations in intensity become negligible, when compared to the average intensity. The second contribution to the intensity fluctuations, which is due to the diffusion in an inhomogeneous excitation profile, also vanishes at high particle concentrations. Any vacancy created by a molecule leaving a position is practically always filled by another molecule moving to that position, so that no net change in the fluorescence intensity occurs. Thus, a constant fluorescence intensity dictates a Poissonian photon count distribution.

Influence of Molecular Brightness

We used three different fluorophores, each with its own brightness parameter $\epsilon$, to illustrate the influence of the molecular brightness c on the photon count distribution. Each fluorophore sample was made up to approximately the same concentration to facilitate the comparison of the different histograms. The count distributions are analyzed with the PCH algorithm and are shown together with the fits in FIG. 4. Poisson distributions with the same mean as the average photon counts are displayed as dashed lines for each histogram. The deviation between the tail of the PCH and the Poisson distribution increases with increasing $\epsilon$.

In To maximize the deviation between the photon count distribution and the corresponding Poisson function, one can either reduce the number of molecules within the excitation volume or increase the brightness parameter $\epsilon$ as demonstrated in FIG. 4. The relationship between the super-Poissonian character of the PCH and the molecular brightness $\epsilon$ can be qualitatively understood. The average fluorescence intensity of a molecule in the excitation volume is characterized by the parameter $\epsilon$. A particle with a larger value of $\epsilon$ causes stronger intensity fluctuations as it enters and diffuses through the beam. The increase in the fluorescence intensity fluctuations leads to a further broadening of the PCH. This behavior is a consequence of the averaging of Poisson distributions over a wider intensity range as expressed by Mandel's formula. To quantify this statement, we define the fractional deviation Q, a measure of the deviation between the PCH and the Poisson distribution (Mandel, 1979), $$Q = \frac{\langle \Delta k^2 \rangle - \langle k \rangle}{\langle k \rangle} = \gamma \varepsilon, \quad (33)$$

where $\langle \Delta k^2 \rangle$ and $\langle k \rangle$ are the variance and the expectation value of the photon counts, respectively, and $\gamma$ is the shape factor of the PSF (Thompson, 1991). The fractional deviation Q and the g(0) value of the intensity autocorrelation function (Thompson, 1991), $$g(0) = \frac{\langle \Delta I^2 \rangle}{\langle I \rangle^2} = \frac{\langle \Delta k^2 \rangle - \langle k \rangle}{\langle k \rangle^2} = \frac{\gamma}{\overline{N}}, \quad (34)$$

are closely related. The g(0) value is the ratio of the shape factor $\gamma$ to the average number of molecules $\overline{N}$ inside the PSF. The relationship between the intensity moments and the factorial moments of the photon counts (Teich and Saleh, 1988) allows us to express g(0) by the variance and the average of the photon counts. Thus, the ratio of Q to g(0) determines the average photon counts $\langle k \rangle$, according to eq. 10.

A Poissonian distribution is defined by Q=0, while super-Poissonian distributions require Q>0 and sub-Poissonian distributions mandate Q<0. The molecular brightness largely determines the super-Poissonian character of the PCH, since Q is directly proportional to the parameter $\epsilon$, which depends on the excitation power, the detection efficiency and the molecular species.

Sensitivity of PCH Algorithm

To provide a quantitative description of the deviation of the photon counting histogram from a Poisson distribution, we define the following reduced $\chi_{Poi}^2$ function $$\chi_{Poi}^2(\varepsilon, \overline{N}, M) = \underset{\tilde{k}}{\mathrm{Min}} \left[ \sum_{k=k_{\min}}^{k_{\max}} \left( M \frac{\Pi(k, \varepsilon, \overline{N}) - Poi(k, \tilde{k})}{\sigma_k} \right)^2 \frac{1}{k_{\max} - k_{\min}} \right], \quad (35)$$

where the standard deviation is given by $\sigma_k = (M\Pi(k,\epsilon,\overline{N})(1-\Pi(k,\epsilon,\overline{N})))^{1/2}$. The function $\chi_{Poi}^2$ describes the statistical significance of the deviation of the PCH from a Poisson distribution. If the value of $\chi_{Poi}^2$ is less than or equal to 1 then the statistics are not sufficient to distinguish the data from a Poisson distribution. The larger the value of $\chi_{Poi}^2$, the stronger the deviation between the PCH and the Poisson distribution. Equation 35 requires the minimization of the function with respect to the parameter $\tilde{k}$. Since for most cases the value of $\tilde{k}$ is nearly identical with the average photon counts of the PCH function, $\langle k \rangle = \epsilon \overline{N}$, matching the first moments of the PCH and Poisson function is a good approximation of the function $\chi_{Poi}^2$.

We evaluated $\chi_{Poi}^2$ for a variety of conditions to explore the sensitivity of PCH analysis. The dependence of $\chi_{Poi}^2$ on the average number of molecules $\overline{N}$ for constant molecular brightness $\epsilon$ is shown in FIG. 5. Increasing the number of molecules at low concentrations results first in a steady increase of $\chi_{Poi}^2$, then the function reaches a maximum and decreases monotonically at high particle concentrations. Thus, an optimal concentration exists, where the photon count distribution has a maximal deviation from the Poisson distribution.

We can understand this result intuitively. Increasing the particle concentration leads to smaller amplitude fluctuations g(0), which means that the intensity distribution is approaching a delta function, as already mentioned before. Reducing the number of molecules in the observation volume produces stronger fluctuation amplitudes. However, once the average number of molecules is less than one molecule, the probability that no molecule is found in the observation volume greatly increases. Therefore, except for the case where k=0 the signal to noise ratio of the histogram is markedly reduced. Thus, two effects shape the $\chi_{Poi}^2$ function and lead to a maximum around a particle concentration of one molecule in the observation volume. The function $\chi_{Poi}^2$ is shown in FIG. 5 for two different molecular brightness values to illustrate the influence of $\epsilon$ upon the peak position. For brighter particles, the maximum of the function $\chi_{Poi}^2$ occurs at a lower concentration. An increase in the molecular brightness $\epsilon$ increases the broadening of the PCH and shifts the maximum of $\chi_{Poi}^2$ to lower particle concentrations.

The absolute values of the $\chi_{Poi}^2$ function depend strongly on the brightness parameter. In order to show the two curves on the same graph, the corresponding functions for the larger brightness had to be scaled down to be visible (FIG. 5). The dependence of $\chi_{Poi}^2$ the molecular brightness $\epsilon$ was evaluated for two fixed concentrations ($\overline{N}$=0.01 and 1.2) and both were fit to a straight line, that yielded a decadic logarithm of about 1.75 for both particle concentrations (FIG. 6).

The value of the $\chi_{Poi}^2$ function is directly proportional to the number of data points M taken, and therefore directly proportional to the data acquisition time. If we formally define the square root of the $\chi_{Poi}^2$ function to be a measure of the signal to noise ratio (SNR), then we find, that the SNR of PCH is proportional to the square root of the data acquisition time, and close to linear for the molecular brightness. These conclusions are similar to those by Koppel, where the SNR was derived for the autocorrelation function under the simplifying condition of Gaussian statistic (Koppel, 1974).

The dependence of the SNR on the number of molecules in the excitation volume is related to another study (Kask et al., 1997). There, it was shown that the SNR of the second moment is constant at high particle concentrations, but decreases at low particle concentrations. However, the SNR of the third moment displays a maximum at a concentration of about one particle per observation volume. This behavior of the SNR is also found in the SNR of the PCH, which is not surprising, since all moments are contained in the photon count distribution.

PCH for Multiple Species

Resolving multiple species is an important issue in many biological applications. Biological macromolecules interact with other molecules, and as a consequence of this network of interactions, the complex machinery of life is maintained. FCS has successfully been used to resolve multiple species (Rauer et al., 1996). However, it is generally recognized that resolving two species by the autocorrelation function alone requires a difference in their diffusion coefficients of the order of 2 or larger (Meseth et al., 1999). This poses a severe restriction on the application of the pure autocorrelation approach to many biological systems, since the differences between the diffusion coefficients of biomolecules is often less than a factor of two. The association of two monomer subunits, for example, to form a dimer is a widespread and important biological reaction mechanism (Berland et al., 1996). The increase in the diffusion coefficient for a diner is about 25 percent of the monomer value. Since the diffusion coefficient approximately scales with the cubic root of the molecular mass, a difference in the molecular weight of about a factor of 8 would be required to resolve two components by the autocorrelation function alone. To address this intrinsic shortcoming of the autocorrelation approach two other methods have been introduced in the literature. One is based on higher order autocorrelation functions (Palmer and Thompson, 1987; Palmer and Thompson, 1989) and another is based on higher order moment analysis (Qian and Elson, 1990a; Qian and Elson, 1990b).

Here we introduce a new approach for separating fluorescent species based on the photon counting histogram. The histogram of photon counts is sensitive to the molecular brightness and was discussed in detail for a single species. If two species differ in their molecular brightness, then a molecule of the brighter species entering the observation volume will produce a stronger fluorescent intensity change than the other species. By considering the statistics of these intensity changes, one can deduce the brightness and the average number of molecules of each species. Shot noise caused by the photodetection process is added to these intensity fluctuations. It was shown that the resulting photon counting statistics for multiple species is given by the consecutive convolution of the single species photon counting histograms. While the histogram of a single species requires two parameters, 2r parameters are required to describe the histogram for r species, namely the molecular brightness $\epsilon_i$ and the average number of particles $\overline{N}$ for each species. In the following, we discuss the resolution of two species in detail, consider practical limitations and demonstrate the technique experimentally.

Resolvability of Two Species

We discuss the most difficult case where the two species must be resolved by the histogram alone without any further knowledge. From a practical point of view one wants to know what data acquisition tine and concentrations to choose in order to resolve species of a given brightness. To address this question we calculated the theoretical histograms for different conditions, in order to identify experimentally favorable concentrations and brightness conditions. The theoretically determined two-species PCH function were then fit assuming a single species model and the reduced $\chi^2$ determined. A fit of a two species histogram by a single species model will result in a misfit, which gives rise to systematic residuals. The magnitude of the residuals tells us, whether it is feasible to distinguish between single and multiple species. A reduced $\chi^2$ value of one or less indicates, that the data statistics is not sufficient to resolve the species, while a $\chi^2$ greater than one indicates that more than one species is present. We want to find out which brightness differences can be separated. The brightness for a given species is kept constant during the calculation of the histograms, but the concentration is varied in a systematic manner. For a fixed brightness ratio the results are best represented graphically in the form of a contour plot of the $\chi^2$ surface as a function of the logarithmic concentration of both species. The concentration of each species is expressed in number of molecules within the PSF.

The above has been offered for illustrative purposes only, and is not intended to limit the scope of the invention of the application, which is as defined in the claims below.

REFERENCES

Abramowitz, M., and I. A. Stegun. 1965. Handbook of mathematical functions with formulas, graphs, and mathematical tables. Dover Publications, New York.

Aragon, S. R., and R. Pecora. 1975. Fluorescence correlation spectroscopy and Brownian rotational diffusion. *Biopolymers.* 14:119–137.

Axelrod, D., D. E. Koppel, J. Schlessinger, E. Elson, and W. W. Webb. 1976. Mobility measurement by analysis of fluorescence photobleaching recovery kinetics. *Biophys. J.* 16:1055–69.

Bendat, J. S., and A. G. Piersol. 1971. Random data: Analysis and measurement procedures. Wiley-Interscience, New York.

Berland, K. M., P. T. C. So, Y. Chen, W. W. Mantulin, and E. Gratton. 1996. Scanning two-photon fluctuation correlation spectroscopy: particle counting measurements for detection of molecular aggregation. *Biophys. J.* 71:410–420.

Berland, K. M., P. T. C. So, and E. Gratton. 1995. Two-photon fluorescence correlation spectroscopy: method and application to the intracellular environment. *Biophys. J.* 68:694–701.

Bertolotti, M. 1973. Photon statistics. In Photon correlation and light beating spectroscopy. H. Z. Cummins and E. R. Pike, editors. Plenum Press, New York. 41–74.

Borejdo, J. 1979. Motion of myosin fragments during actin-activated ATPase: fluorescence correlation spectroscopy study. *Biopolymers.* 18:2807–2820.

Chandrasekhar, S. 1943. Stochastic problems in physics and astronomy. *Rev. Mod. Phys.* 15:1–89.

Chen, Y. 1999. Analysis and applications of fluorescence fluctuation spectroscopy. University of Illinois at Urbana-Champaign, Urbana.

Chen, Y., J. D. Müller, P. T. C. So, and E. Gratton. 1999. The photon counting histogram in fluorescence fluctuation spectroscopy. *Biophys. J.* (submitted).

Eggeling, C., J. R. Fries, L. Brand, R. Gunther, and C. A. M. Seidel. 1998. Monitoring Conformational Dynamics of a Single Molecule By Selective Fluorescence Spectroscopy. *Proceedings of the National Academy of Sciences of the United States of America.* 95:1556–1561.

Ehrenberg, M., and R. Rigler. 1974. Rotational Brownian motion and fluorescence intensity fluctuations. *Chem. Phys.* 4:390–401.

Eigen, M., and R. Rigler. 1994. Sorting single molecules: application to diagnostics and evolutionary biotechnology. *Proc. Natl. Acad. Sci. USA.* 91:5740–5747.

Elson, E. L., and D. Magde. 1974. Fluorescence correlation spectroscopy. I. Conceptual basis and theory. *Biopolymers.* 13:1–27.

Feller, W. 1957. An introduction to probability theory and its applications. John Wiley & Sons, Inc., New York.

Gardiner, C. W. 1985. Handbook of stochastic methods. Springer, N.Y.

Jakeman, E., G. Parry, E. R. Pike, and P. N. Pusey. 1978. The Twinkling of Stars. *Contemp. Phys.* 19:127–145.

Johnson, J. B. 1928. Thermal agitation of electricity in conductors. *Phys. Rev.* 32:97–109.

Kask, P., R. Günter, and P. Axhausen. 1997. Statistical accuracy in fluorescence fluctuation experiments. *Eur. Biophys. J.* 25:163–169.

Kask, P., P. Piksarv, M. Pooga, and Ü. Mets. 1989. Separation of the rotational contribution in fluorescence correlation experiments. *Biophys. J.* 55:213–220.

Kinjo, M., and R. Rigler. 1995. Ultrasensitive hybridization analysis using fluorescence correlation spectroscopy. *Nucleic Acids Res.* 23:1795–1799.

Koppel, D. E. 1974. Statistical accuracy in fluorescence correlation spectroscopy. *Phys. Rev. A.* 10:1938–1945.

Koppel, D. E., D. Axelrod, J. Schlessinger, E. L. Elson, and W. W. Webb. 1976. Dynamics of fluorescence marker concentration as a probe of mobility. *Biophys. J.* 16:1315–1329.

Koppel, D. E., F. Morgan, A. E. Cowan, and J. H. Carson. 1994. Scanning concentration correlation spectroscopy using the confocal laser microscope. *Biophys. J.* 66:502–507.

Luke, Y. L. 1969. The special functions and their approximations. Academic Press, New York.

Luria, S. E., and M. Delbrück. 1943. Mutations of bacteria from virus sensitivity to virus resistance. *Genetics.* 28:491–511.

Magde, D., E. Elson, and W. W. Webb. 1972. Thermodynamic fluctuations in a reacting system: measurement by fluorescence correlation spectroscopy. *Phys. Rev. Lett.* 29:705–708.

Magde, D., E. L. Elson, and W. W. Webb. 1974. Fluorescence correlation spectroscopy. II. An experimental realization. *Biopolymers.* 13:29–61.

Mandel, L. 1958. Fluctuations of photon beams and their correlations. *Proc. Phys. Soc.* 72:1037–1048.

Mandel, L. 1979. Sub-Poissonian photon statistics in resonance fluorescence. *Optics Letters.* 4:205–207.

Mehta, C. L. 1970. Theory of photoelectron counting. In Progress in Optics. E. Wolf, editor. North-Holland Publishing Company, Amsterdam. 375–440.

Meseth, U., T. Wohland, R. Rigler, and H. Vogel. 1999. Resolution of fluorescence correlation measurements. *Biophysical Journal.* 76:1619–1631.

Palmer, A. G. d., and N. L. Thompson. 1987. Molecular aggregation characterized by high order autocorrelation in fluorescence correlation spectroscopy. *Biophys J.* 52:257–70.

Palmer, A. G. d., and N. L. Thompson. 1989. High-order fluorescence fluctuation analysis of model protein clusters. *Proc Natl Acad Sci USA.* 86:6148–52.

Petersen, N. O., D. C. Johnson, and M. J. Schlesinger. 1986. Scanning fluorescence correlation spectroscopy. II. Application to virus glycoprotein aggregation. *Biophys. J.* 49:817–20.

Qian, H. 1990. On the statistics of fluorescence correlation spectroscopy. *Biophys Chem.* 38:49–57.

Qian, H., and E. L. Elson. 1990a. Distribution of molecular aggregation by analysis of fluctuation moments. *Proc. Natl. Acad. Sci. USA.* 87:5479–5483.

Qian, H., and E. L. Elson. 1990b. On the analysis of high order moments of fluorescence fluctuations. *Biophys. J.* 57:375–80.

Qian, H., and E. L. Elson. 1991. Analysis of confocal laser-microscope optics for 3-D fluorescence correlation spectroscopy. *Appl. Opt.* 30:1185–1195.

Rauer, B., E. Neumann, J. Widengren, and R. Rigler. 1996. Fluorescence correlation spectrometry of the interaction kinetics of tetramethylrhodamin alpha-bungarotoxin with torpedo californica acetylcholine receptor. *Biophys. Chem.* 58:3–12.

Rigler, R., Ü. Mets, J. Widengren, and P. Kask. 1993a. Fluorescence correlation spectroscopy with high count rate and low background: analysis of translational diffusion. *Eur. Biophys. J.* 22:169–175.

Rigler, R., J. Widengren, and Ü. Mets. 1993b. Interactions and kinetics of single molecules as observed by fluorescence correlation spectroscopy. In Fluorescence Spectroscopy: New Methods and Applications. O. S. Wolfbeis, editor. Springer, Berlin. 13–24.

Risken, H. 1970. Statistical properties of laser light. In Progress in Optics. E. Wolf, editor. North-Holland Publishing Company, Amsterdam. 241–294.

Saleh, B. 1978. Photoelectron statistics, with applications to spectroscopy and optical communications. Springer-Verlag, Berlin.

Schwille, P., F. J. Meyer-Almes, and R. Rigler. 1997. Dual-color fluorescence cross-correlation spectroscopy for multicomponent diffusional analysis in solution. *Biophys J.* 72:1878–86.

Slater, L. J. 1966. Generalized hypergeometric functions. Cambridge University Press, Cambridge.

Snyder, D. L. 1975. Random point processes. Wiley-Interscience, New York.

Teich, M. C., and B. E. A. Saleh. 1988. Photon bunching and antibunching. In Progress in Optics. E. Wolf, editor. North-Holland Publishing Company, Amsterdam. 1–104.

Thompson, N. L. 1991. Fluorescence correlation spectroscopy. In Topics in fluorescence spectroscopy. J. R. Lakowicz, editor. Plenum, New York. 337–378.

Thompson, N. L., and D. Axelrod. 1983. Immunoglobulin surface-binding kinetics studied by total internal reflection with fluorescence correlation spectroscopy. *Biophys J.* 43:103–114.

Weissman, M., H. Schindler, and G. Feher. 1976. Determination of molecular weights by fluctuation spectroscopy: application to DNA. *Proc. Natl. Acad. Sci. USA.* 73:2776–80.

Weissman, M. B. 1981. Fluctuation spectroscopy. *Ann. Rev. Phys. Chem.* 32:205–232.

Weissman, M. B. 1988. 1/f noise and other slow, nonexponential kinetics in condensed matter. *Reviews of Modern Physics.* 60:537–571.

Widengren, J., Ü. Mets, and R. Rigler. 1995. Fluorescence Correlation Spectroscopy of Triplet States in Solution—a Theoretical and Experimental Study. *J. Phys. Chem.* 99:13368–13379.

That which is claimed:

1. The method of performing fluorescence correlation spectroscopy, which comprises:

acquiring a fluorescence measurement over time from a sample in the form of electronic raw data; electronically storing said raw data; and processing said raw data using a first algorithm without erasing said electronically stored raw data.

2. The method of claim 1 which comprises subsequently reprocessing said stored raw data using a second algorithm different from said first algorithm.

3. The method of claim 2 in which said raw data is acquired using a photon-mode technique.

4. The method of claim 1 in which said raw data is acquired using a photon-mode technique.

* * * * *

UNITED STATES PATENT AND TRADEMARK OFFICE
CERTIFICATE OF CORRECTION

PATENT NO. : 6,794,659 B2
DATED : September 21, 2004
INVENTOR(S) : Barbieri et al.

It is certified that error appears in the above-identified patent and that said Letters Patent is hereby corrected as shown below:

<u>Column 26,</u>
Line 17, add:
5. The method of claim 1 which the molecular brightness of a plurality of said species is determined from said fluorescence measurement.
6. The method of claim 1 in which the fluorescence measurement is taken from a sample volume of no more than 10 femtoliters.
7. The method of performing fluorescence correlation spectroscopy which comprises: acquiring a fluorescence measurement from a sample over time in the form of electronic raw data;
electronically storing said raw data;
obtaining a histogram of photon counts from said electronic raw data;
processing said raw data using a first algorithm without erasing said electronically stored raw data, said processing comprising the step of deriving the molecular brightness of at least one molecular species in said sample; and determining the concentration of said species.
8. The method of claim 9 which comprises subsequently reprocessing said stored raw data using a second algorithm different from said first algorithm.
9. The method of claim 10 in which said raw data is acquired using a photon-mode technique.
10. The method of claim 9 in which said raw data is acquired using a photon-mode technique.
11. The method of claim 12 in which the molecular brightness of a plurality of said species is determined from said fluorescence measurement.
12. The method of claim 9 in which the fluorescence measurement is taken from a sample volume of no more than 10 femtoliters.
13. The method of claim 14 which the molecular brightness of a plurality of said species is determined from said fluorescence measurement.
14. The method of claim 15 which comprises subsequently reprocessing said stored raw data using a second algorithm different from said first algorithm.

UNITED STATES PATENT AND TRADEMARK OFFICE
CERTIFICATE OF CORRECTION

PATENT NO. : 6,794,659 B2
DATED : September 21, 2004
INVENTOR(S) : Barbieri et al.

It is certified that error appears in the above-identified patent and that said Letters Patent is hereby corrected as shown below:

Column 26 (cont'd),
15. The method of claim 9 in which the molecular brightness of a plurality of said species is determined from said fluorescence measurement.

Signed and Sealed this

Thirtieth Day of May, 2006

JON W. DUDAS
*Director of the United States Patent and Trademark Office*